US008916091B2

(12) United States Patent
Koehl et al.

(10) Patent No.: US 8,916,091 B2
(45) Date of Patent: Dec. 23, 2014

(54) METHOD FOR PRODUCING SEMI-FINISHED PRODUCTS FROM NITI SHAPE MEMORY ALLOYS

(75) Inventors: Manuel Koehl, Duesseldorf (DE); Martin Bram, Juelich (DE); Berthold Coenen, Hueckelhoven (DE); Hans Peter Buchkremer, Heinsberg (DE); Detlev Stoever, Niederzier (DE)

(73) Assignee: Forschungszentrum Juelich GmbH, Juelich (DE)

( * ) Notice: Subject to any disclaimer, the term of this patent is extended or adjusted under 35 U.S.C. 154(b) by 762 days.

(21) Appl. No.: 12/733,867
(22) PCT Filed: Aug. 27, 2008
(86) PCT No.: PCT/DE2008/001427
§ 371 (c)(1),
(2), (4) Date: Apr. 30, 2010
(87) PCT Pub. No.: WO2009/043323
PCT Pub. Date: Apr. 9, 2009

(65) Prior Publication Data
US 2010/0310407 A1 Dec. 9, 2010

(30) Foreign Application Priority Data
Oct. 4, 2007 (DE) .......................... 10 2007 047 523

(51) Int. Cl.
B22F 3/15 (2006.01)
(52) U.S. Cl.
USPC ................................. 419/49; 419/23; 419/33
(58) Field of Classification Search
USPC ............... 75/243; 623/1.2; 419/37, 49, 23, 33
IPC ... A61F 6/225; A61L 31/16; A61M 2025/0076; C22C 1/0491; B22F 1/0003,1/0007
See application file for complete search history.

(56) References Cited

U.S. PATENT DOCUMENTS 2,849,789 A * 9/1958 Thomson ........................ 75/243
4,410,488 A 10/1983 Gessinger et al.
(Continued)

FOREIGN PATENT DOCUMENTS

| DE | 3520266 C1 * | 1/1987 |
|---|---|---|
| EP | 0 045 985 | 2/1982 |
| WO | WO-02/085561 | 10/2002 |

OTHER PUBLICATIONS

Mentz et al. "Influence of heat treatment treatments on the mechanical properties of high-quality Ni-rich NiTi produced by powder metallurgy methods", Materials Science and Engineering A 481-482 (2008) 630-634, Available on line Jun. 6, 2007.*

(Continued)

*Primary Examiner* — Weiping Zhu
(74) *Attorney, Agent, or Firm* — Jordan and Hamburg LLP

(57) ABSTRACT

Disclosed is a method for producing semi-finished products from a shape memory alloy, particularly an NiTi shape memory alloy, wherein a powder is first produced from a shape memory alloy, and subsequently the powder is divided into a coarse fraction and a fine fraction in a separating cut T. While the fine fraction is required, in particular, for the production of a first semi-finished product, employing the metal injection molding (MIM) method, the coarse fraction can be used for the production of a second semi-finished product, employing the hot isostatic pressing (HIP) method. The advantages of the invention can be summarized as follows. The MIM method for producing semi-finished products from a shape memory alloy is qualitatively improved and more cost-effective to implement if the coarse fraction that is typically obtained during powder production, but not used for the MIM process, can advantageously be supplied to a further process, in this case the HIP process. Due to the use of particularly fine powder, the semi-finished products produced by way of the MIM method have an advantageous, powder-metallurgical microstructure. In particular, the alloying elements are distributed particularly homogeneously in these semi-finished products, casting flaws or segregations do not usually occur, no anisotropy of the structure occurs as a result of the processing steps, and ternary alloys can be processed, which due to the mechanical properties thereof, cannot be processed by way of conventional forming methods.

3 Claims, 3 Drawing Sheets

(56) References Cited

U.S. PATENT DOCUMENTS

| | | | |
|---|---|---|---|
| 5,284,329 A * | 2/1994 | Hohman et al. | 266/202 |
| 5,508,116 A | 4/1996 | Barrett | |
| 2001/0007953 A1 * | 7/2001 | Duerig et al. | 623/1.2 |
| 2004/0146424 A1 | 7/2004 | Nelles et al. | |

OTHER PUBLICATIONS

J. Ments et al: "Influence of heat treatments on themechanical properties of high-quality Ni-rich NiTi produced by powder metallurgical methods" Materials Science and Engineering A, vol. 481-482, 2008, pp. 630-634, XP002508745 p. 630-p. 631.

Zheng H X et al: "Powder metallurgical production of TiNiNb and TiNiCu shape memory alloys by combination of pre-alloyed and elemental powders" Journal of Alloys and Compounds, Elsevier Sequoia, Lausanne, CH, vol. 463+ No. 1-2, Sep. 8, 2008, pp. 250-256, XP023176014 ISSN: 0925-8388 [retrieved on Jul. 23, 2008] p. 250-p. 251.

C. Trepanier, T.K. Leung, M. Tabrizian, L'H. Yahia, J.-G. Bienvenu, J.-F. Tanguay, D.L. Piron, L. Bilodeau: "Preliminary investigation of the effects of surface treatments on biological response to shape memory NiTi stents" J. Biomed. Mater. Res., vol. 48, 1999, pp. 165-171, XP002508746 Figure 1.

* cited by examiner

METHOD FOR PRODUCING SEMI-FINISHED PRODUCTS FROM NITI SHAPE MEMORY ALLOYS

The invention relates to semi-finished products made of a nickel-titanium shape memory alloy, and in particular to the production thereof.

BACKGROUND OF THE INVENTION

The term semi-finished products denotes the general concept of prefabricated shapes made from raw materials, such as sheet metal, bars, tubes, and coils. In metal working, semi-finished products constitute by far the most common delivery form for feedstocks made of metals and plastics.

A typical characteristic of semi-finished products is that they are not, in general, used in the original dimension or size. The first processing step typically involves a blank, from which the required material section is severed, using a suitable separating method (such as cutting).

Two manufacturing methods, in particular, are known for the production of semi-finished products, which is to say metal injection molding (MIM) and hot isostatic pressing (HIP). Both of these two methods have the advantage associated with the powder-metallurgical production of components or semi-finished products, in so much as the need to finish the components is low.

Metal injection molding is a method for producing minute and small metallic parts. The method combines two known manufacturing technologies which actually have little to do with each other, these being plastic injection molding and metal sintering. The MIM method comprises four partial steps, consisting of spray mixing of the molding compound, injection molding, removing the binder, and sintering. In the first step, a suitable, very fine metal powder is mixed with a binder to form a moldable starting material. Contrary to conventional pressing and sintering, in which densities of 90% of the theoretical material density are typically achieved, the metal injection molding method achieves densities between 96% and 100% of the theoretical material density. In this way, material properties are advantageously attained which largely correspond to those of parts manufactured from solid metal.

Furthermore, when modified, the MIM method can also be used to produce particularly porous semi-finished products by employing spacers. The porosity can advantageously be set between 10 and 80% by volume.

Since, in general, the components or semi-finished products manufactured by way of the MIM method do not require any metal finishing, the more difficult a material usually is to process, the greater the advantages of the metal injection molding method are. This method is therefore particularly suited to stainless steels, soft magnetic alloys, iron/nickel materials, as well as tool steels and special alloys, such as nickel-titanium shape memory alloys.

Shape memory alloys are metals which return to their original shape after deformation, once they are heated to a certain temperature. In the process, they can develop significant forces. Possible applications for shape memory alloys include micromanipulators and robot actuators, which can imitate the smooth movements of human muscles. In reinforced concrete structures, sensors made of shape memory alloys can be used, for example, to detect cracks in the concrete or corrosion in the steel reinforcement bars and to counteract internal stresses.

Previously, shape memory alloys that are based on the intermetallic phase NiTi have preferably been produced by a fusion metallurgy process. Conventional shaping by machining of metallurgically-fused semi-finished products made of NiTi materials, however, is limited because, in the martensitic state, the alloys exhibit a high elongation at break and therefore have poor machining properties. As a result, the finishing of components produced by way of fusion-metallurgy processes involves high time expenditure and high tooling wear.

Previously, employing the metal injection molding method for NiTi shape memory alloys frequently failed because there was a need for, not only an economical production process, but also an end product having the low impurity levels required for shape memory properties. Thus, a challenge in the manufacture of NiTi components by way of metal injection molding (MIM) is that of minimizing the oxygen and carbon contents to as great an extent as possible. High impurity levels result in reduced sintering activity for the metal powders and worsen the material properties in the sintered component (due to embrittlement or the like). In addition, another important requirement for producing NiTi shape memory alloys is the precise and reproducible adjustment of the alloy composition. Even minor variations in the composition produce considerable variations in the characteristic properties (such as the transformation temperatures).

During production of the powder, in general, particles having a generally large particle size distribution are obtained, including a portion of coarser particles. Gas atomization by which the powder is obtained is presently known to produce mean particle sizes $d_{50}$ as small as approximately 50 µm or even smaller.

While the use of particularly fine starting powders has the advantage, in terms of process engineering, that they exhibit excellent moldability, they are generally also associated with the risk of higher impurity levels resulting from the crucible material that is used, which has proven particularly disadvantageous for NiTi shape memory alloys comprising a third alloying element.

As a result, producing the powder by way of crucible-free (impurity-free) melting, using induction and atomization according to the EIGA (electrode induction melting gas atomization) process, is suited for particularly pure and low-impurity powders, such as those which are required for the production of semi-finished products from a shape memory alloy. However, the disadvantage is that the particle fraction of the powder produced in this way having a particle diameter larger than 45 µm usually constitutes more than 65% by weight. Separating the required fine fraction, and failing to use the separated coarse fraction, as was conventional, therefore made the use of this material for the production of semi-finished products by way of the MIM method very expensive.

For applications requiring particularly fine particles, these particles can frequently only be obtained by separating the coarse fraction from the powder that has been produced. For example, separating cuts of $d_{97}$ between 2 and 120 µm can be attained by using fine sifters.

The second method for producing semi-finished products is hot isostatic pressing (HIP). This method is a development in the manufacturing engineering industry, wherein powders and solids, in particular ceramics and metals, are hot-pressed and sintered at the same time. During hot isostatic pressing (HIP), powdery or porous materials are uniformly compressed entirely without binders by applying high temperatures (lower than the melting temperature of the material) and isostatic pressure of several hundred MPa. For this method, for example, use is made of finely atomized materials from the melting bath, which ensure high-quality microstructures, resulting in a high degree of freedom in terms of selection of the alloy. Inert gases are used as the pressure transfer medium during hot isostatic pressing. Powders or highly porous materials are encapsulated in the process, while components having closed pores can also be compressed by hot isostatic pressing without being encapsulated. This results in structures that are homogeneous to an extent that is almost impossible to achieve using other methods. Components produced by way of an HIP method are extremely dense (up to 100% of theoretical density) and have isotropic properties. Advantageously, a composite component produced from different materials can be achieved with this method.

A major disadvantage of this technique is that it is very complex and therefore associated with very high manufacturing costs, particularly when low dimensional tolerances are required. The primary field of application is the redensification of sintered, metallic and ceramic workpieces for the aerospace industry, the automotive industry, or medical implants.

SUMMARY OF THE INVENTION

The object of the invention is to create semi-finished products, particularly semi-finished products made from a shape memory alloy, in a cost-effective manner and to provide a cost-effective method for producing these semi-finished products.

The objectives of the invention are achieved by a method for producing semi-finished products and by semi-finished products made in this way. Advantageous embodiments of the method and of the semi-finished products will be apparent from the following description of the invention.

The invention is based on the concept that the method for producing semi-finished products by way of hot isostatic pressing can be improved in terms of costs, in that the starting powder used is precisely that portion of the particles that is typically produced during the production of powders for an MIM method, but which is not utilized. While the powder size used, in particular the coarser portion, has virtually no effect on the quality attained during hot isostatic pressing (HIP), the use of the particularly fine particle portion is of tremendous advantage for the MIM process.

This means that through the skillful combination of two methods, which is to say the metal injection molding (MIM) method on one hand, and the hot isostatic pressing (HIP) method for producing a semi-finished product on the other hand, particularly advantageous cost efficiency can be achieved, in that the two methods employ different portions of the manufacturing process for the powder.

Producing the powder by way of a method that is complex per se is advantageous if, after separating the fine fraction required for the MIM method, the coarse fraction can be used in a meaningful manner, in this case for producing semi-finished products by way of the HIP method. Using the separated coarser powders for the HIP method is hardly a disadvantage, because the powder, prior to pressurization, is easy to compact, and the pressurization parameters do not significantly vary from those that would be used when producing the semi-finished product from a powder fraction having a normal distribution.

Impurity-free melting and atomization (EIGA) has proven to be a particularly suitable method for producing powders from highly reactive metals and alloys. The particle size in particular, or the particle size distribution, is used for characterizing powders. The particle size distribution results from particle size analysis. Ultimately, it is no more than a frequency distribution in the form of a bar chart. The percentage part by volume of the particles is plotted against the equivalent sized diameter, or alternatively the particle size (x-axis). The particle size distribution is frequently also represented as a cumulative curve.

In practice, the particle size distribution is usually determined by sifting (grading curve), sedimentation, or visual methods. A variety of other methods are available, which are limited to certain substances or size ranges. In some contexts, disperse systems are identified by mean values.

Using the EIGA method, in general, powders having a mean equivalent diameter $d_{50}$ of approximately 80 µm can be produced. For subsequent use of this powder in an MIM process, however, frequently only the fine fraction of such a powder mixture, for example, the powder smaller than 45 µm, is employed, and frequently and advantageously, even smaller than 25 µm. The coarse fraction having a mean particle size that is greater than 45 µm, which sometimes constitutes more than 65% by weight of the powder mixture that is produced, often goes unused, but this makes the overall process quite expensive.

Within the scope of the present invention, it was found that precisely this coarse fraction is best utilized in an HIP method for producing semi-finished products. Previously, powder mixtures having a corresponding particle size distribution, which is to say in terms of the distribution in which they are obtained from the corresponding powder production step, were used during the shaping step for hot isostatic pressing.

According to the invention, first a nearly impurity-free powder is produced from a nickel-titanium base alloy. The gas atomization (EIGA) method, for example, is a suitable manufacturing method for this material and the corresponding particle size distribution. The material can, for example, generally be produced in an appropriate particle size distribution, wherein the portion having a mean particle size of larger than 45 µm constitutes a weight component of more than 65%.

In a further step, the fine fraction of the material below a specific separating limit is separated, and only the coarse fraction is used for producing semi-finished products by way of the HIP method. The fine fraction is advantageously used for an MIM process. The separating cut as such can be implemented using conventional methods, wherein a separating cut in the range between 1 and 100 µm, particularly between 10 and 50 µM, is considered meaningful for the method according to the invention.

The NiTi shape memory alloys should be mentioned in particular as shape memory alloys suitable for the method. It is possible to use both the pure NiTi alloys, and also ternary or quaternary NiTi-based alloys. In addition to NiTi as the base constituent, these ternary or quaternary alloys comprise small amounts of at least one further alloying element X from the group (X=Cu, Nd, Hf, Zr, Pt or Pd). In the literature, for example, the following admixing ranges are disclosed: for Nb between 4.5 and 9 atom %, for Cu between 5 and 20 atom %, for Hf between 9.5 and 20 atom %, for Zr between 1 and 50 atom %, and for Pt up to a maximum of 10 atom %.

The advantages of the invention can be summarized as follows:
  The MIM method for producing semi-finished products from a shape memory alloy is more lucrative and more cost-effective to implement.
  The semi-finished products produced in this way have a powder-metallurgical microstructure, and in particular the alloying elements are distributed particularly homogeneously,
  casting flaws or segregations do not usually occur,
  no anisotropy of the structure occurs as a result of the processing steps, ternary alloys can be processed, which due to the mechanical properties thereof cannot be processed by way of conventional forming methods.

DESCRIPTION OF THE PREFERRED EMBODIMENT

The invention will be described in more detail hereinafter based on an exemplary embodiment of the production of a semi-finished product by way of the HIP method, without thereby limiting the scope of protection.

Figure 1:
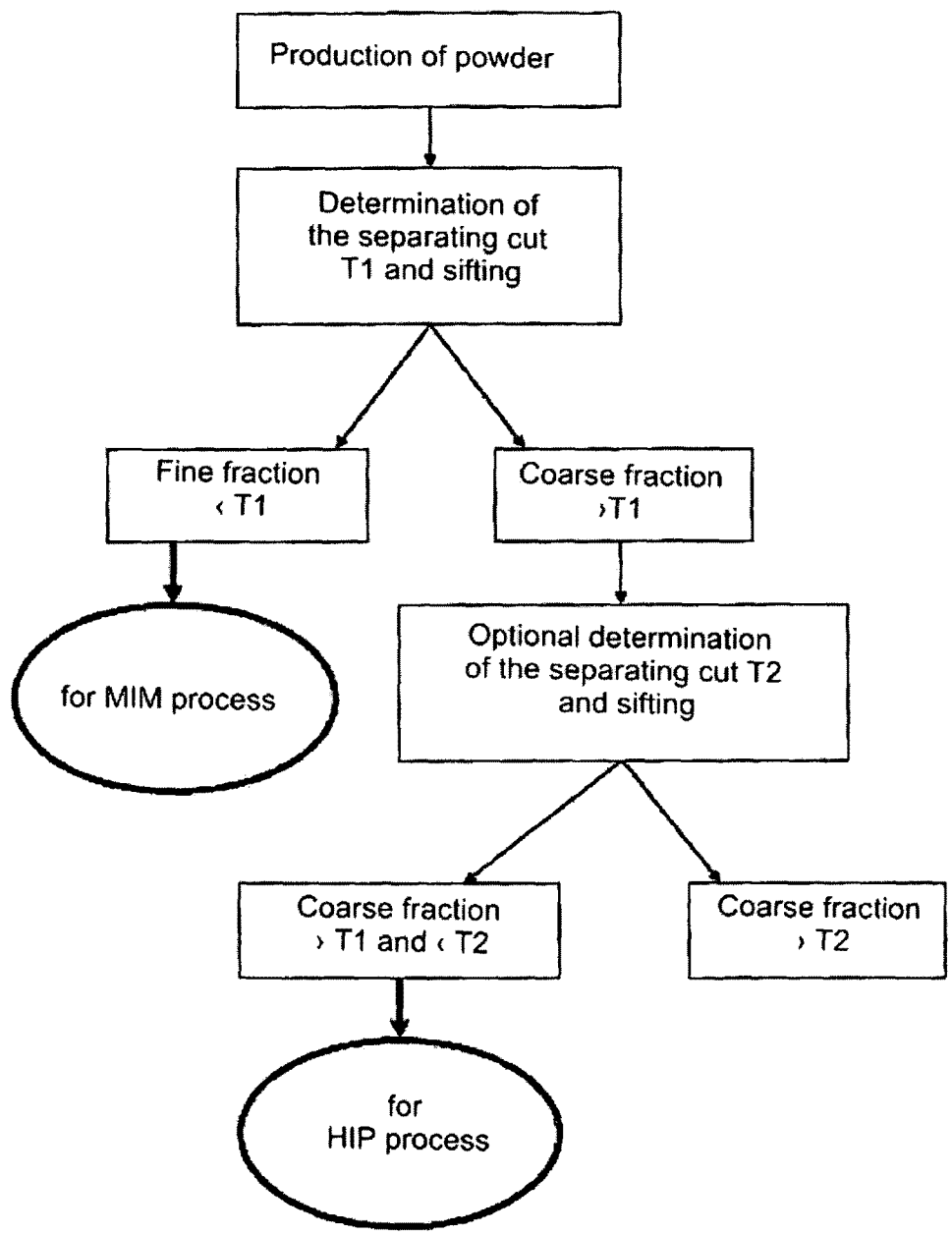
FIG. 1 is a flow chart showing the method according to one embodiment of the invention.

The basic method is apparent from the flow chart shown in FIG. 1.

A powder was produced from the NiTi shape memory alloy, and four fractions were sifted off from the entire batch: a) <25 μm, b) 25 to 45 μm, c) 45 to 100 μm and d) >100 μm. The yield from fractions a)+b), which is to say the particles having a mean particle diameter smaller than 45 μm, was approximately 35% by weight.

Figure 2:
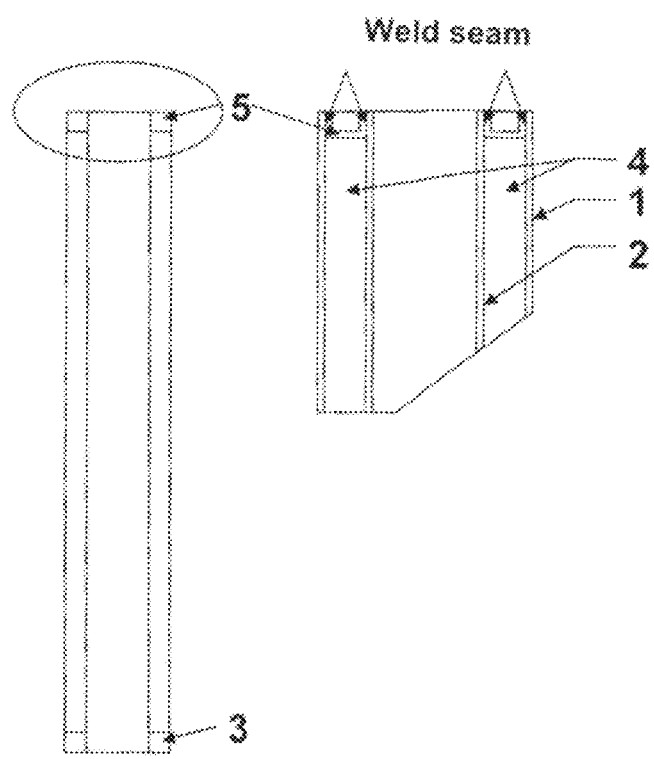
FIG. 2 shows an HIP capsule.

The coarse fraction c) comprising nearly spherical powders having a mean diameter greater than 45 μm and smaller than 100 μm was transferred into an HIP capsule, the geometry of which is apparent from FIG. 2. The fraction d) greater than 100 μm was set aside, because it usually also comprises very large coarse particles, also referred to as flakes. The HIP capsule is an outer tube (1) having an inner tube (2) disposed centrally therein. Both tubes are fixed by a lower cover (3) and welded together.

The powder (4) was filled between the inner and outer tubes and compressed in order to achieve the highest possible tap density. For this purpose, the capsule, which was initially filled loosely, including an attachment, was exposed to vertical drop impacts having low frequencies on an eccentric-driven table. This device, which is referred to as a compression volumeter, is usually employed for determining a volume and following compression, however in this case it is only intended to compress the packing to the tap density. The degree of compression depends on the elasticity of the sub-surface and the height of the fall (fall delay) and the number of drop impacts. Thereafter, the upper cover (5) of the HIP capsule was welded by electron beam welding under vacuum, or after evacuating the capsule.

Figure 3:
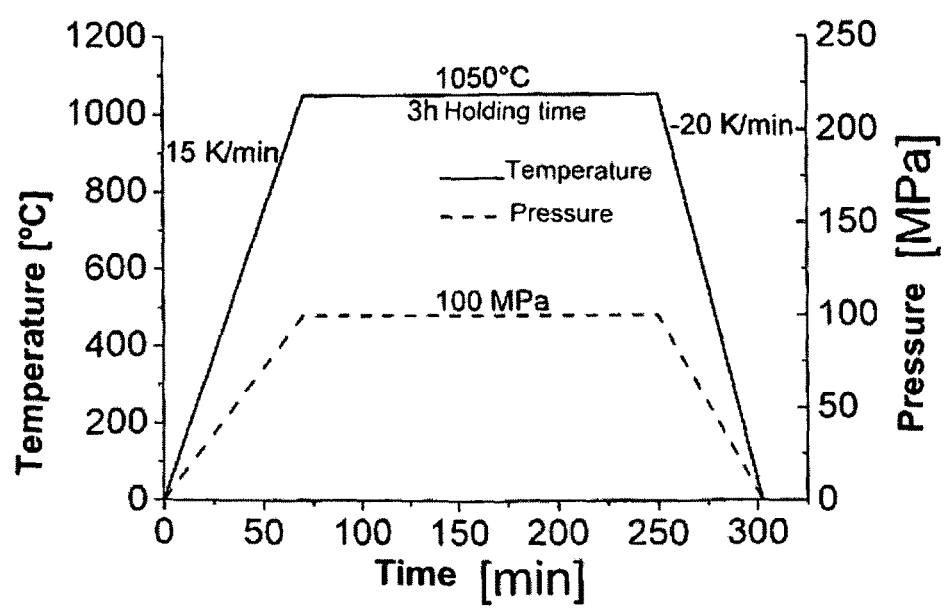
FIG. 3 is a graph showing the recompressed NiTi exposed to a defined pressure and temperature profile.

The tube comprising the precompressed NiTi was then exposed to a defined pressure and temperature profile (HIP cycle) in a suspended manner, which is apparent from FIG. 3. The suspension of the HIP capsules advantageously caused a higher dimensional stability of the samples.

As an alternative to the aforementioned test setup according to FIG. 2, the inner tube can also be made of solid material for increased dimensional stability of the NiTi or NiTi—X during the HIP process.

Thereafter, the stainless steel cap of the capsule was unscrewed or drilled out and the tube was drawn in order to obtain the semi-finished product according to the invention.

By employing additional steps, this semi-finished product, for example, can be further processed in the conventional manner into stents or clamping rings, particular shape memory alloys (NiTi—X, X=Cu, Nb, Hf, Zr, Pt, Pd) which previously were difficult to machine being of interest as materials for the clamping rings.

The invention claimed is:

1. A method for producing a semi-finished product for producing a stent, the semi-finished product being obtained from a shape memory alloy, comprising the following steps:
producing a powder from the shape memory alloy by gas atomization,
separating the produced powder based on particle size into a first group of particles having a size range up to a first size and a second group having a size range greater than said first size, said first size being at least 75 μm;
separating the second group of particles into a third group of particles having a size range between said first size and a second size and a fourth group of particles having a size range greater than the second size, said second size being between 100 μm and 150 μm, the third group having a distribution of particles between said first size and said second size;
filling the third group of particles into an hot isostatis pressing (HIP) capsule comprising an outer tube having an inner tube disposed centrally therein and compacting said fraction, and
subjecting the HIP capsule to an HIP process, thereby producing the semi-finished product, said semi-finished product being tubular,
wherein the shape memory alloy is a NiTi alloy having a ratio of Ni to Ti between 45 atom % to 55 atom % and 55 atom % to 45 atom %, the NiTi alloy comprising a further alloying element selected from Cu, Nb, Zr, Pt or Pd.

2. The method according to claim 1, wherein the shape memory alloy has a ratio of Ni to Ti between 48.5 atom % to 51.5 atom % and 51 atom % to 49 atom %.

3. The method according to claim 1, wherein the powder is produced by way of an EIGA (electrode induction melting gas atomization) method.

* * * * *